(12) United States Patent
Chebiyyam et al.

(10) Patent No.: US 7,241,895 B2
(45) Date of Patent: Jul. 10, 2007

(54) POLYMORPHIC FORMS OF 5-[4-[2-[N-METHYL-N-(2-PYRIDYL) AMINO[ETHOXY]BENZYL] THIAZOLIDINE-2,4-DIONE MALEATE AND PROCESS FOR THEIR PREPARATION

(75) Inventors: Prabhakar Chebiyyam, Hyderabad (IN); Ramabhadra Sarma Mamillapalli, Hyderabad (IN); Vyas Krishnamurthi, Hyderabad (IN); Vishnuvardhan Reddy Seella, Hyderabad (IN); Om Reddy Gaddam, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 146 days.

(21) Appl. No.: 10/381,512

(22) PCT Filed: Sep. 25, 2001

(86) PCT No.: PCT/US01/29896

§ 371 (c)(1),
(2), (4) Date: Nov. 7, 2003

(87) PCT Pub. No.: WO02/26737

PCT Pub. Date: Apr. 4, 2002

(65) Prior Publication Data

US 2004/0068116 A1   Apr. 8, 2004

(30) Foreign Application Priority Data

Sep. 26, 2000 (IN) .............................. 805/MAS/00

(51) Int. Cl.
*C07D 417/12* (2006.01)
(52) U.S. Cl. .................................. 546/269.7
(58) Field of Classification Search ................ 514/342; 546/269.7
See application file for complete search history.

(56) References Cited

U.S. PATENT DOCUMENTS

| | | | | |
|---|---|---|---|---|
| 5,741,803 A | * | 4/1998 | Pool et al. .................. | 514/342 |
| 6,515,132 B2 | * | 2/2003 | Vyas ........................ | 546/268.7 |
| 2005/0014798 A1 | * | 1/2005 | Turchetta et al. ........... | 514/342 |

FOREIGN PATENT DOCUMENTS

| | | |
|---|---|---|
| EP | 0306228 | 3/1989 |
| EP | 002191825 | 11/1998 |
| WO | 9405659 | 3/1994 |
| WO | 9727191 | 7/1997 |
| WO | 9741120 | 11/1997 |
| WO | 00/64892 | * 11/2000 |
| WO | 00/64893 | * 11/2000 |
| WO | 0064896 | 11/2000 |

OTHER PUBLICATIONS

Brittain, Polymorphism in Pharmaceutical Solids—Drugs and the Pharmaceutical Sciences, NY Marcel Deckker, 1999, pp. 125-358.*
Chemical & Engineering News, Feb. 2003, pp. 32-35.*
US Pharmacopia, 1995, pp. 1843-1844.*
Halbein et al., J. Pharm. Sci., 58 (1969) pp. 911-928.*
Concise Encyclopedia Chemistry, NY: Walter de Gruyter, 1994, pp. 872-873.*
Wall, "Pharmaceutical Applications of Drug, etc.," Pharmaceutical Manufacturing, vol. 3 (2) pp. 32-34, Feb. 1986.*
Brittain et al., "Polymorphism in Pharmaceutical Solids", NY Marcel Dekker et al., (1999), pp. 1-2,125-181,183-226, 228-278.*
Parks D, J.; Tomkinson, N.C.O.; Villeneuve M.S.; Blanchard S.G.: "Differential Activity Of Risiglitazone Enantiomers At PPAR" Bioorganic & Medicinal Chemistry Letters, vol. 8, 1998, pp. 3657-3658.

* cited by examiner

*Primary Examiner*—Patricia L. Morris
(74) *Attorney, Agent, or Firm*—Milagros A. Cepeda; Robert A. Franks (57) ABSTRACT

This invention relates to novel polymorphic/pseudopolymorphic forms of 5-[4-[2[N-methyl-N-(2-pyridyl)amino] ethoxy]benzyl]thiazolidine-2,4-dione maleate having formula (I). The invention also relates to a pharmaceutical composition comprising the novel polymorphic form or their mixture and a pharmaceutically acceptable carrier. The polymorphic forms of the present invention are more active, as antidiabetic agent, than the hitherto known 5-[4-[2-[N-(2-methyl-N-(2-pyridyl)amino]ethoxy]benzyl] thiazolidine-2,4-dione maleate (I)

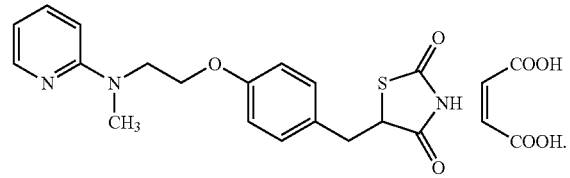

16 Claims, 9 Drawing Sheets

POLYMORPHIC FORMS OF 5-[4-[2-[N-METHYL-N-(2-PYRIDYL) AMINO[ETHOXY]BENZYL] THIAZOLIDINE-2,4-DIONE MALEATE AND PROCESS FOR THEIR PREPARATION

FIELD OF THE INVENTION

This invention relates to novel polymorphic/pseudopolymorphic forms of 5-[4-[2-[N-methyl-N-(2-pyridyl)amino]ethoxy]benzyl]thiazolidine-2,4-dione maleate and its stereoisomers having formula (I). The invention also relates to a pharmaceutical composition comprising the novel polymorphic form or their mixture and a pharmaceutically acceptable carrier. The polymorphic forms of the present invention are more active, as antidiabetic agent, than the hitherto known 5-[4-[2-[N-methyl-N-(2-pyridyl)amino]ethoxy]benzyl]thiazolidine-2,4-dione maleate.

(I)

The present invention also relates to a process for the preparation of various polymorphic/pseudopolymorphic 5-[4-[2-[N-methyl-N-(2-pyridyl)amino]ethoxy] benzyl] thiazolidine-2,4-dione maleate, having the formula (I) shown below. The polymorphic forms prepared by the process of the present invention are more active, as an antidiabetic agent.

The polymorphic forms of 5-[4-[2-[N-methyl-N-(2-pyridyl)amino]ethoxy]benzyl]thiazolidine-2,4-dione maleate, of formula (I) defined above of the present invention reduce blood glucose and has beneficial effect on coronary heart disease and atherosclerosis.

Out of the many drugs available for the treatment of diabetic ailments, the thiazolidine dione derivatives are very prominent and are considered as much superior effective constituents compared to the sulphonyl ureas. 5-[4-[2-[N-methyl-N-(2-pyridyl)amino]ethoxy]benzyl]thiazolidine-2, 4-dione maleate, one such thiazolidinedione which exhibited euglycemic effect, was reported in the year 1988 by Beecham group England (EP 0306228A1) and created interest in the field, ever since.

The novel polymorphic forms of 5-[4-[2-[N-methyl-N-2-pyridyl)amino]ethoxy]benzyl]thiazolidine-2,4-dione maleate, of formula (I) defined above of the present invention are useful in reducing body weight and for the treatment and/or prophylaxis of diseases such as hypertension, coronary heart disease, atherosclerosis, stroke, peripheral vascular diseases and related disorders. The novel polymorphic forms of 5-[4-[2-[N-methyl-N-(2-pyridyl) amino]ethoxy]benzyl] thiazolidine-2,4-dione maleate, of formula (I) of the present invention can be used for the treatment of certain renal diseases including glomerulonephritis, glomerulosclerosis, nephrotic syndrome, hypertensive nephrosclerosis and nephropathy. The novel polymorphic Forms of 5-[4-[2-[N-methyl-N-(2-pyridyl)amino]ethoxy]benzyl]thiazolidine-2, 4-dione maleate, of formula (I) are also useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. These novel polymorphic forms of 5-[4-[2-[N-methyl-N-(2-pyridyl)amino] ethoxy]benzyl]thiazolidine-2,4-dione maleate, of formula (I) may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The novel polymorphic forms of 5-[4-[2-[N-methyl-N-(2-pyridyl) amino]ethoxy]benzyl]thiazolidine-2,4-dione maleate, of formula (I) of the present invention are useful in the treatment and/or prophylaxis of the above said diseases in combination/con-comittant with one or more HMG CoA reductase inhibitors, hypolipidemic/hypolipoproteinemic agents such as fibric acid derivatives, nicotinic acid, cholestyramine, colestipol, probucol.

BACKGROUND OF THE INVENTION

The latest trend that has, of late, crept into the pharmaceutical industry is the studies on polymorphism in drugs and the difference in the activity of different polymorphic forms of a given drug. By the term polymorphism we mean to include different physical forms, crystal forms, crystalline/liquid crystalline/non-crystalline (amorphous) forms. This has especially become very interesting after observing that many antibiotics, antibacterials, tranquilizers etc., exhibit polymorphism and some/one of the polymorphic forms of a given drug exhibit superior bio-availability and consequently show much higher activity compared to other polymorphs. Sertraline, Frentizole, Ranitidine, Sulfathiazole, Indomethacine etc. are some of the important examples of pharmaceuticals which exhibit polymorphism. Polymorphism in drugs is a topic of current interest and is evident from the host of patents being granted. To cite a few, U.S. Pat. No. 5,700,820 discloses six polymorphic forms of Troglitazone, U.S. Pat. No. 5,248,699 discusses about five polymorphic forms of Sertraline hydrochloride while EP 014590 describes four polymorphic forms of Frentizole. EP 490648 and EP 022527 also deal with the subject of polymorphism in drugs.

European Patent No. 0306338, International publication No. WO 94/25026 and U.S. patent application Ser. No. 5,646,169 describe that the relative configurations of the diastereomers have been determined by x-ray crystallographic analysis and that the crystal and molecular structure of the 5-[4-[2-[N-methyl-N-(2-pyridyl)amino]ethoxy]benzyl]thiazolidine-2,4-dione maleate is under preparation. The report does not touch upon the possibility/observation that 5-[4-[2-[N-methyl-N-(2-pyridyl)amino]thoxy]enzyl]thiazolidine-2,4-dione maleate exists in different polymorphic forms. There is no published literature regarding such an observation till date. Polymorphism in drugs is a topic of current interest and is evident from the host of patents being granted to cite a few U.S. Pat. No. 5,248,699 discusses about five polymorphic forms of Sertraline hydrochloride while EP 014590, describes four polymorphic forms of Frentizole EP 490648 and EP 022527, six polymorphic forms of Troglitazone WO 97/27191 also deal with the subject of polymorphism in drugs. The fact that polymorphism in 5-[4-[2-[N-methyl-N-(2-pyridyl) amino]ethoxy]benzyl] thiazolidine-2,4-dione maleate has not been studied earlier coupled with the current interest in the field of polymorphism in drugs prompted us to take-up this investigation our observations and results from the subject matter of the present invention.

With a view to prevent/cure the chronic complications of diabetes, research is being conducted round the world in recent times. 5-[4-[2-[N-methyl-N-(2-pyridyl)amino] ethoxy]benzyl]thiazolidine-2,4-dione maleate is being considered today as one of the most effective anti-diabetic drugs which as a multi-purpose activity not only acting on diabetes itself but also on the reduction of the triglycerides and also on the accompanying complications mentioned above. Indeed the said 5-[4-[2-[N-methyl-N-(2-pyridyl)amino] ethoxy]benzyl]thiazolidine-2,4-dione maleate is emerging as the second drug candidate of euglycemic class of antidiabetic agents.

With an objective to develop novel polymorphic forms for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetes complications thereof, for the treatment of diseases wherein insulin resistance is the pathophysiological mechanism and for the treatment of hypertension, with better efficacy, potency and lower toxicity, we focused our research to develop new polymorphic forms effective in the treatment of the above mentioned diseases. Effort in this direction has led to polymorphic forms having the formula (I).

Another objective of the present invention is to provide polymorphic forms of 5-[4-[2-[N-methyl-N-(2-pyridyl) amino]ethoxy]benzyl]thiazolidine-2,4-dione maleate, their stereoisomers, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Another objective of the present invention is to provide novel polymorphic forms of 5-[4-[2-[N-methyl-N-(2-pyridyl)amino]ethoxy]benzyl]thiazolidine-2,4-dione maleate, their stereoisomers, pharmaceutically acceptable solvates and pharmaceutical compositions containing them or their mixtures having enhanced activities, without toxic effect or with reduced toxic effect.

Yet another objective of the present invention to provide a process for the preparation of novel polymorphic forms of 5-[4-[2-[N-methyl-N-(2-pyridyl)amino]ethoxy]benzyl]thiazolidine-2,4-dione maleate, their stereoisomers, pharmaceutically acceptable solvates.

Still another objective of the present invention is to provide pharmaceutical compositions containing novel polymorphic forms of 5-[4-[2-[N-methyl-N-(2-pyridyl) amino]ethoxy]benzyl]thiazolidine-2,4-dione maleate, solvates or their mixtures in combination with suitable carriers, solvents, diluents and other media normally employed in preparing such compositions.

SUMMARY OF THE INVENTION

The present invention relates to an observation that 5-[4-[2-[N-methyl-N-(2-pyridyl)amino]ethoxy]benzyl]thiazolidine-2,4-dione maleate exhibits polymorphism, which has not been reported till date. The polymorphic Forms I, II, III and IV are obtained from different solvents like ethanol, acetone, methanol and 1,4-dioxane respectively.

From powder X-ray diffraction studies Forms I, II, III and IV are found to be crystalline in nature.

DSC of the polymorphic Form I shows melting endotherm at 100.53° C. Form II dislays endotherm at 127.67° C. Form m exhibits melting endotherm at 126.41° C. and Form IV exhibits endotherm at 125.39° C.

All these polymorphic forms were proved to be identical in solution as evident from Nuclear Magnetic Resonance (NMR), Ultra Violet (UV) & Mass spectral data. On the other hand, solid state techniques like Differential Scanning Calorimetry (DSC), Powder X-Ray Diffractometry (XRD) and Infra Red spectroscopy (IR) revealed the difference among these forms.

BRIEF DESCRIPTION OF THE FIGURES

X-ray powder diffraction pattern has been obtained on a Rigaku D/Max 2200 model diffractometer equiped with horizontal gonimometer in Θ/2 Θ geometry. The copper K α(λ=1.5418A) radiation was used and the sample was scanned between 3–45 degrees 2Θ.

Differential scanning calorimeter was performed on a Shimadzu DSC-50 equipped with a controller. The data was collected on to a Pentium PC using a Shimadzu TA-50 software. The samples weighed in aluminum cells were heated from room temperature to 220° C. at a heating rate of 5° C./min. The empty aluminum cell was used as a reference. Dry nitrogen gas was purged through DSC cell continuously throughout the analysis at a flow rate of 30 ml/min.

DETAILED DESCRIPTION OF THE INVENTION

Figure 1:
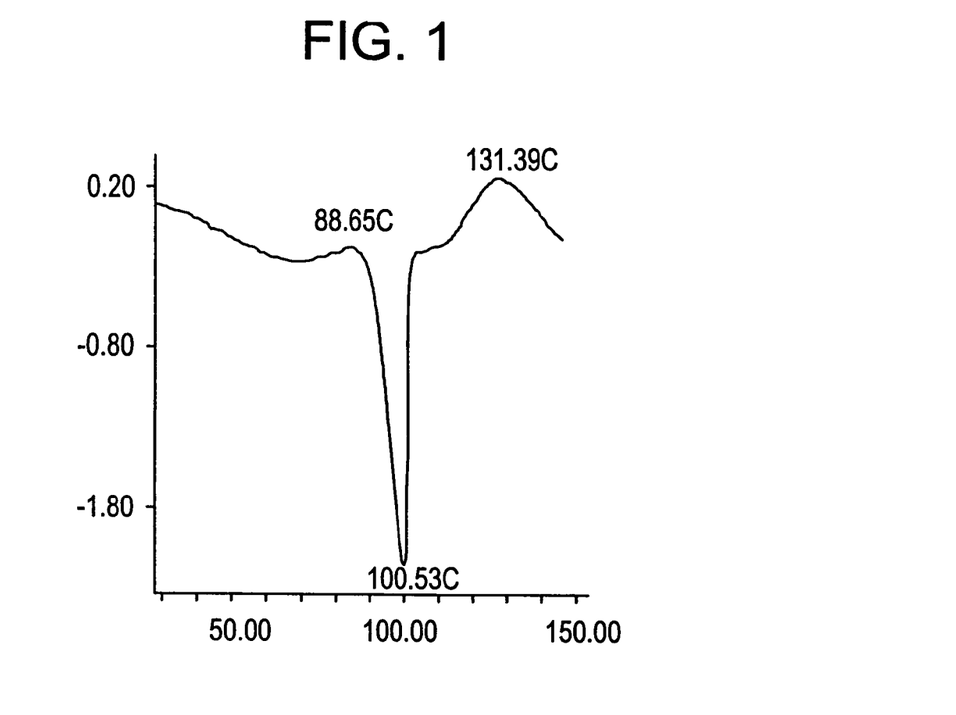
FIG. 1 is a characteristic differential scanning calorimetric thermogram of Form I
Figure 5:
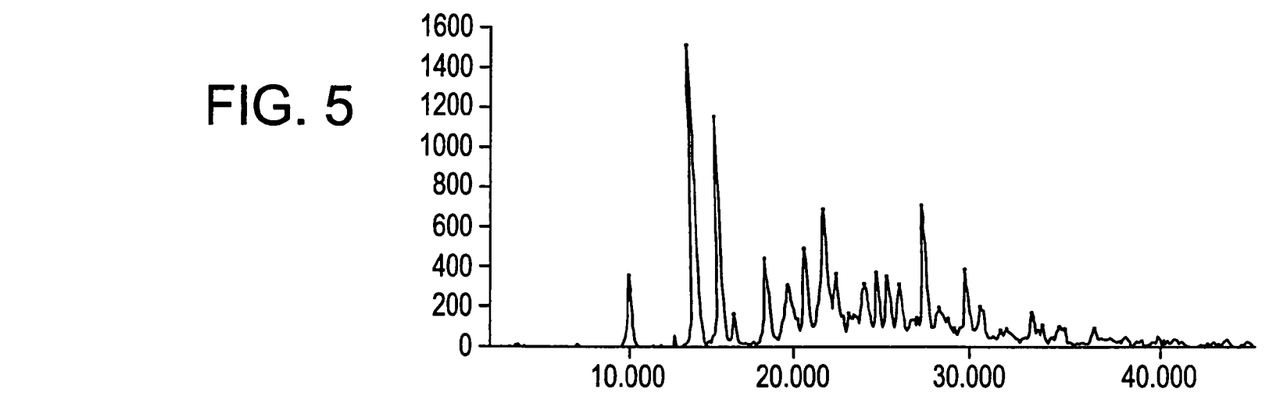
FIG. 5 is a characteristic X-ray diffraction pattern of Form I
Figure 10:
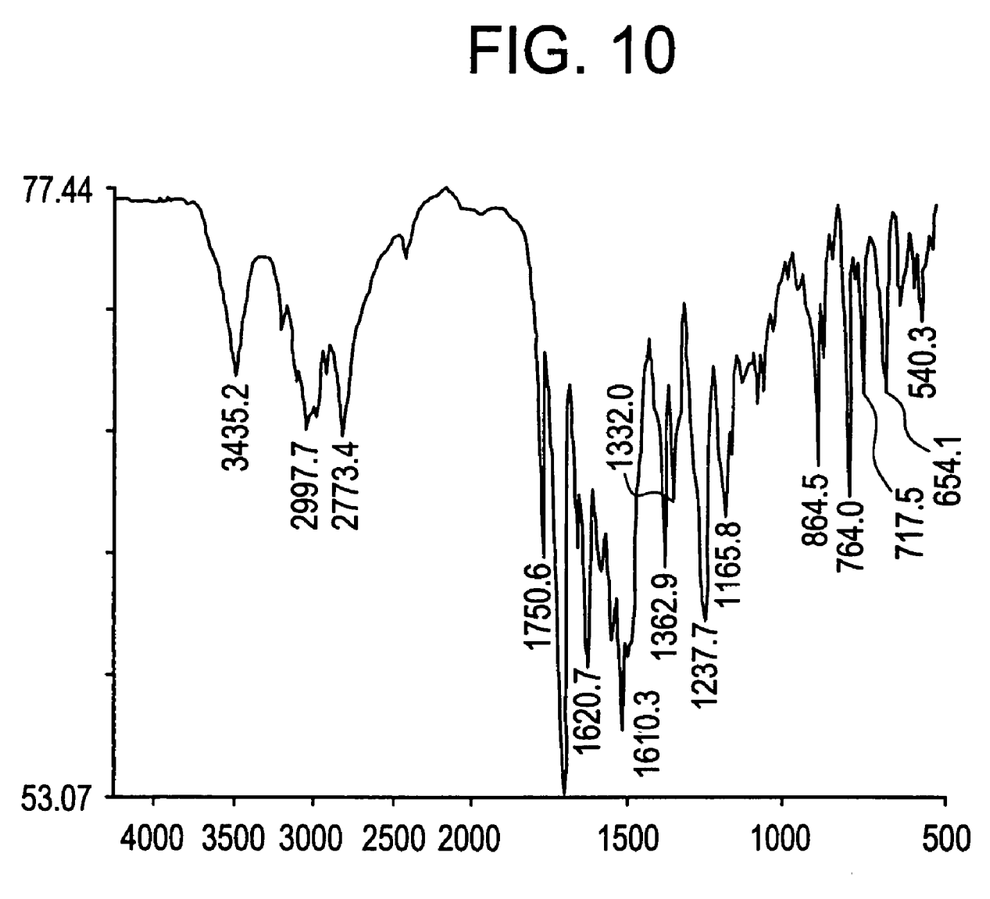
FIG. 10 is a characteristic infrared absorption spectrum of Form I in potassium bromide.

According to a feature of the present invention, there is provided a novel polymorphic Form-I of 5-[4-[2-[N-methyl-N-(2-pyridyl)amino]ethoxy]benzyl]thiazolidine-2,4-dione maleate, and its stereoisomers having the formula I which is characterized by the following data:

DSC endotherm at 100.53° C. (on set at 88.65° C.) (FIG. 1).

X Ray powder diffraction (2Θ): 10.90, 14.54, 15.96, 18.46, 18.60, 19.76, 20.72, 21.84, 22.36, 22,46, 23.90, 24.04, 24.72, 25.30, 25.98, 27.44, 29.70 (FIG. 5).

IR (cm$^{-1}$): 3435 (m), 2997 (w), 2773 (m), 1750 (m), 1701 (s), 1620 (m), 1510 (m), 1362 (m), 1332 (m), 1237 (s), 1165 (m), 864 (s), 764 (s), 717 (m), 654 (m), 540 (w), FIG. (10).

Figure 2:
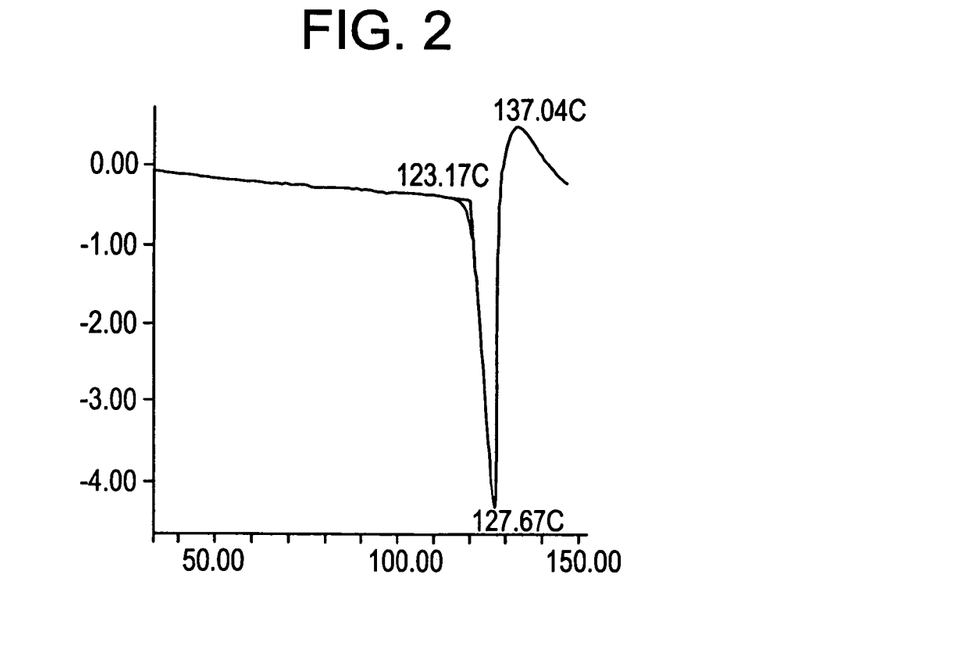
FIG. 2 is a characteristic differential scanning calorimetric thermogram of Form II
Figure 6:
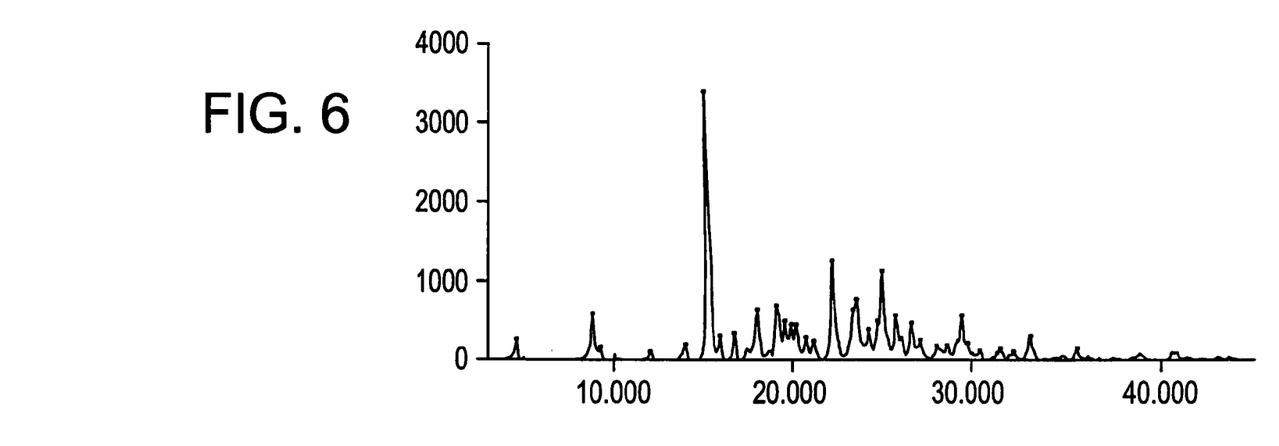
FIG. 6 is a characteristic X-ray diffraction pattern of Form II
Figure 11:
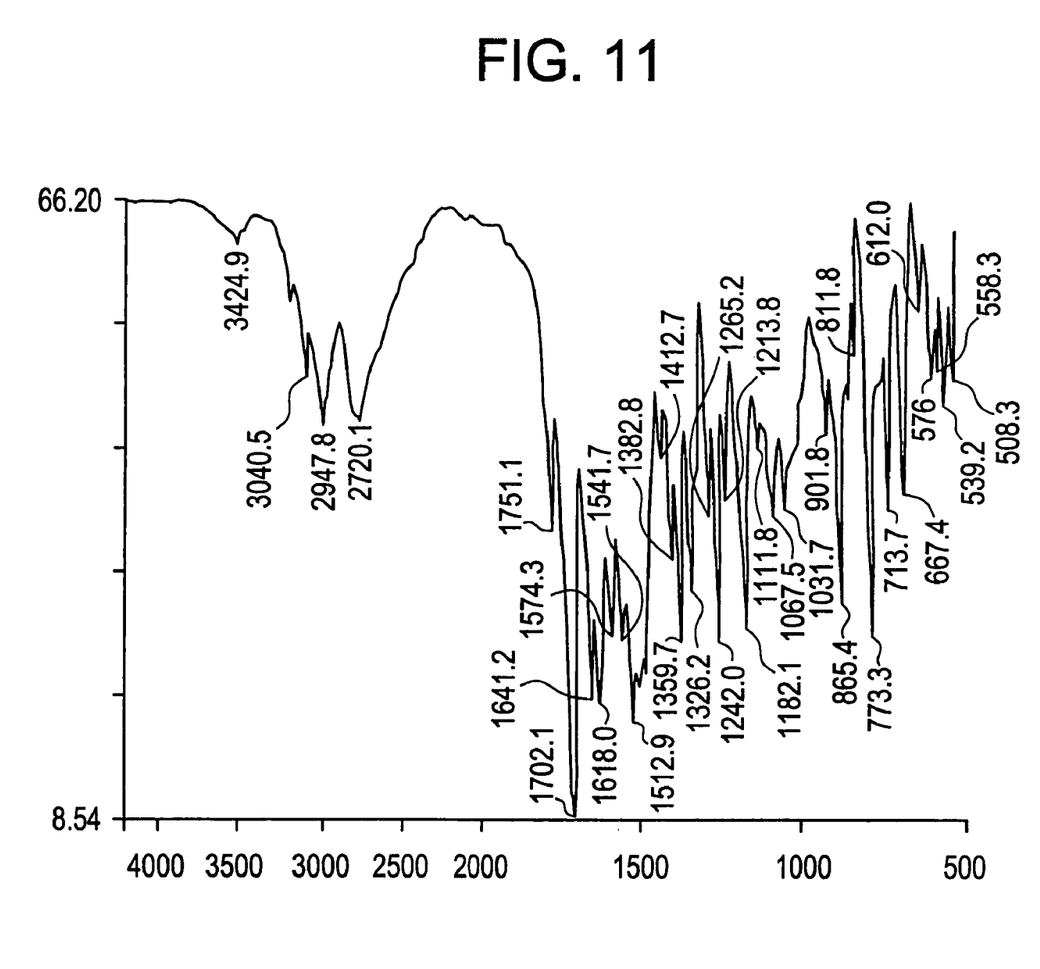
FIG. 11 is a characteristic infrared absorption spectrum of Form II in potassium bromide.

According to another feature of the present invention, there is provided a novel polymorphic Form-II of 5-[4-[2-[N-methyl-N-(2-pyridyl)amino]ethoxy]benzyl]thiazolidine-2,4-dione maleate, and its stereoisomers having the formula I which is characterized by the following data:

DSC: Endotherm at 127.67° C. (on set at 123.17° C.) FIG. 2.

XRD (2Θ): 8.90, 15.40, 18.06, 19.20, 22.30, 23.40, 23.62, 24.80, 25.10, 25.84, 26.72, 27.18, 29.30, 29.54, 29.84, 33.26 (FIG. 6).

IR: 3424 (w), 3040 (w), 2947 (m), 2720 (m), 1751 (m), 1702 (s), 1641 (m), 1618 (m), 1574 (w), 1541 (w), 1412 (w), 1382 (w), 1359 (m), 1326 (m), 1265 (w), 1242 (s), 1213 (w), 1162 (s), 1067 (w), 1031 (w), 865 (s), 773 (s), 713 (s), 667 (m), 576 (w), 539 (m), (FIG. 11).

Figure 3:
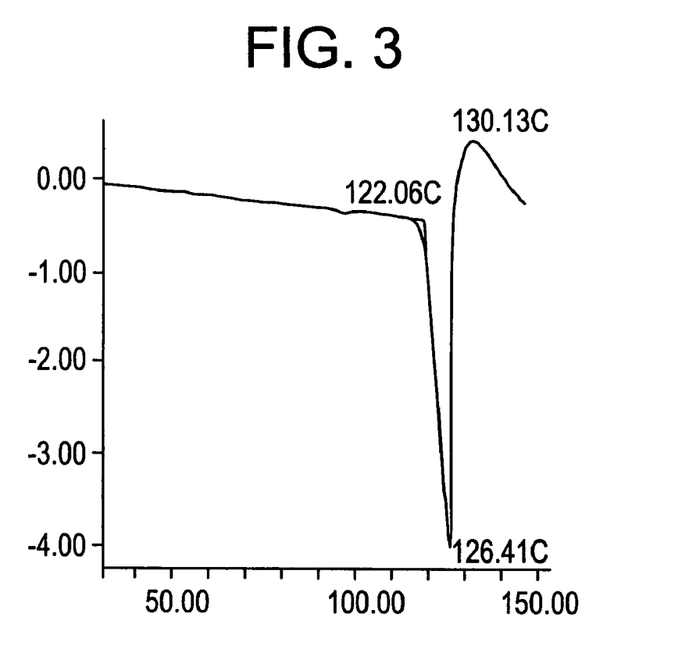
FIG. 3 is a characteristic differential scanning calorimetric thermogram of Form III
Figure 7:
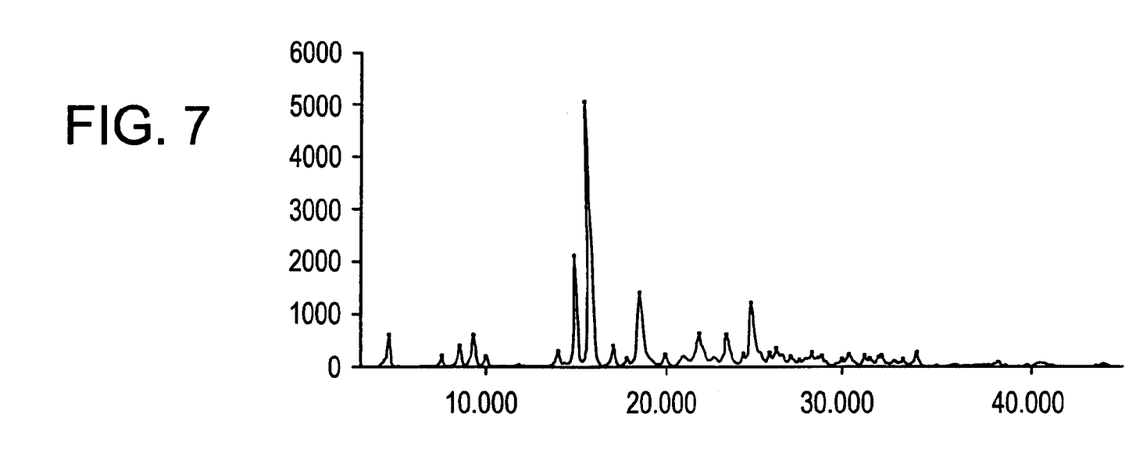
FIG. 7 is a characteristic X-ray diffraction pattern of Form III
Figure 12:
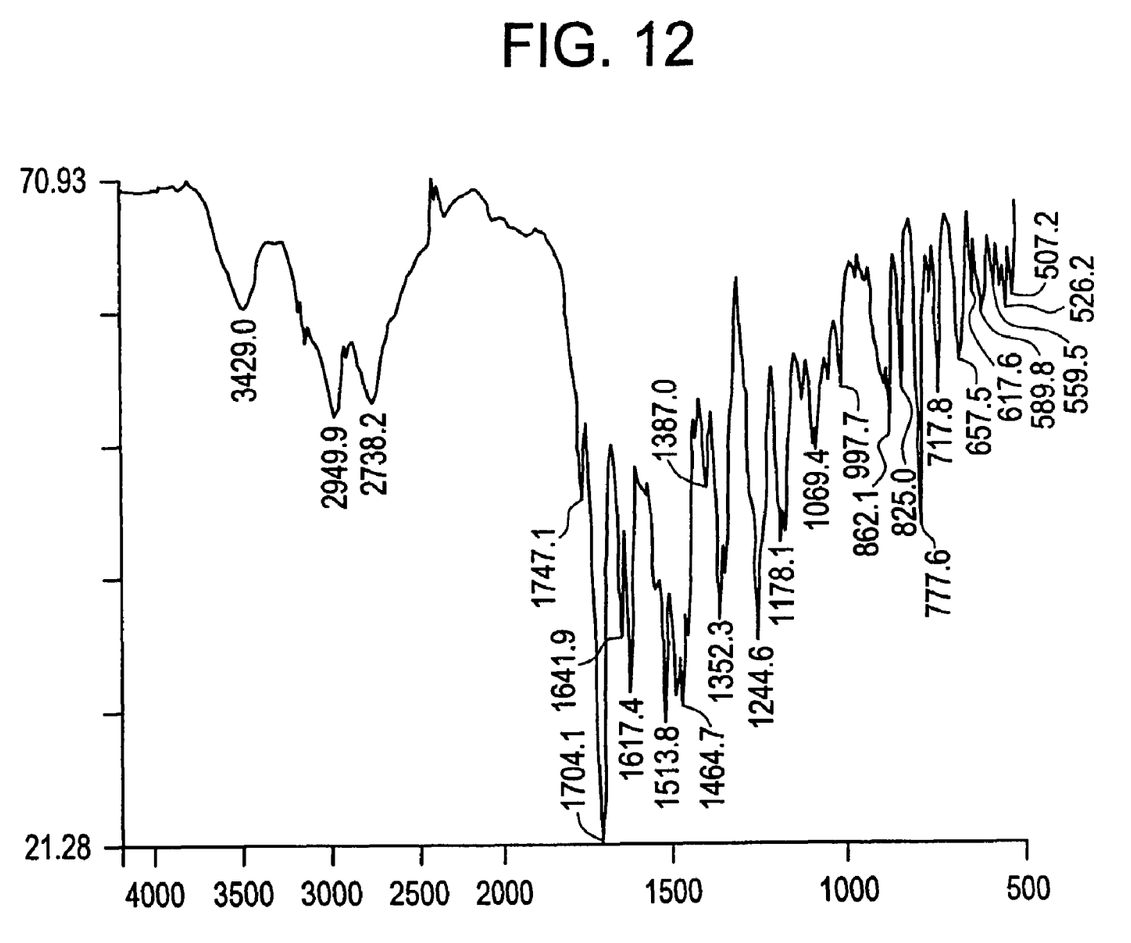
FIG. 12 is a characteristic infrared absorption spectrum of Form III in potassium bromide.

According to yet another feature of the present invention, there is provided a novel polymorphic Form-III of 5-[4-[2-[N-methyl-N-2-pyridyl)amino]ethoxy]benzyl]thiazolidine-2,4-dione maleate and its stereoisomers having the formula I which is characterized by the following data:

DSC: Endotherm at 126.41° C. (on set at 122.06° C.) (FIG. 3).

XRD (2Θ): 4.60, 8.46, 9.24, 14.98, 15.86, 17.02, 18.60, 21.92, 23.50, 25.00, 25.44, 26.00, 26.38, 28.34, 33.90 (FIG. 7).

IR: 3429 (m), 2949 (m), 2738 (m), 1747 (w), 1704 (s), 1641 (m), 1617 (m), 1513 (s), 1464 (m), 1352 (m), 1244 (s), 1178 (s), 1069 (m), 862 (w), 777 (s), 717 (m), 657 (m) 589 (w) (FIG. 12).

Figure 4:
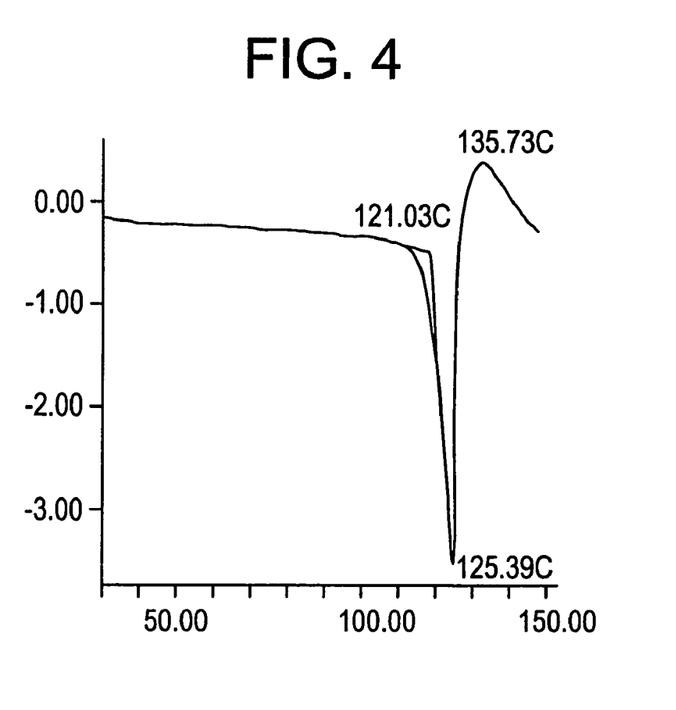
FIG. 4 is a characteristic differential scanning calorimetric thermogram of Form IV
Figure 8:
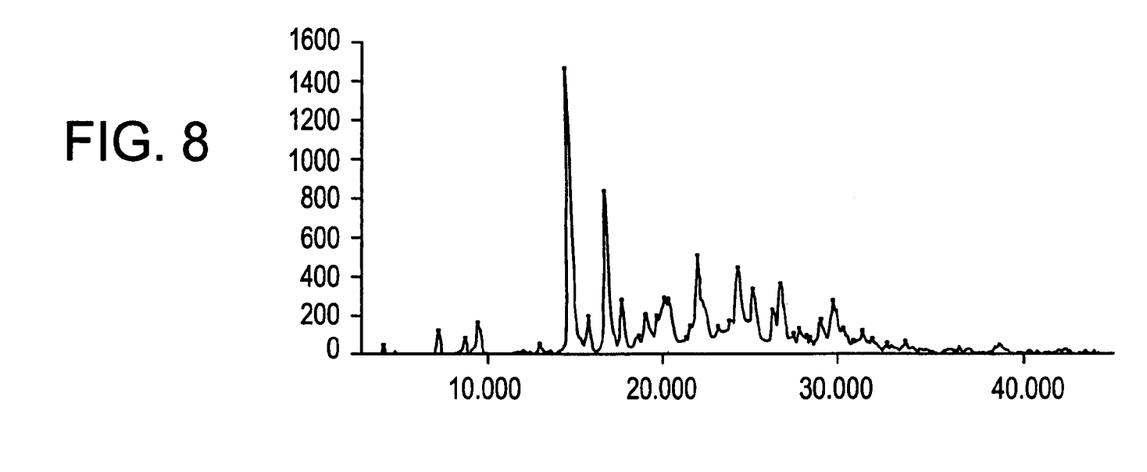
FIG. 8 is a characteristic X-ray diffraction pattern of Form IV
Figure 9:
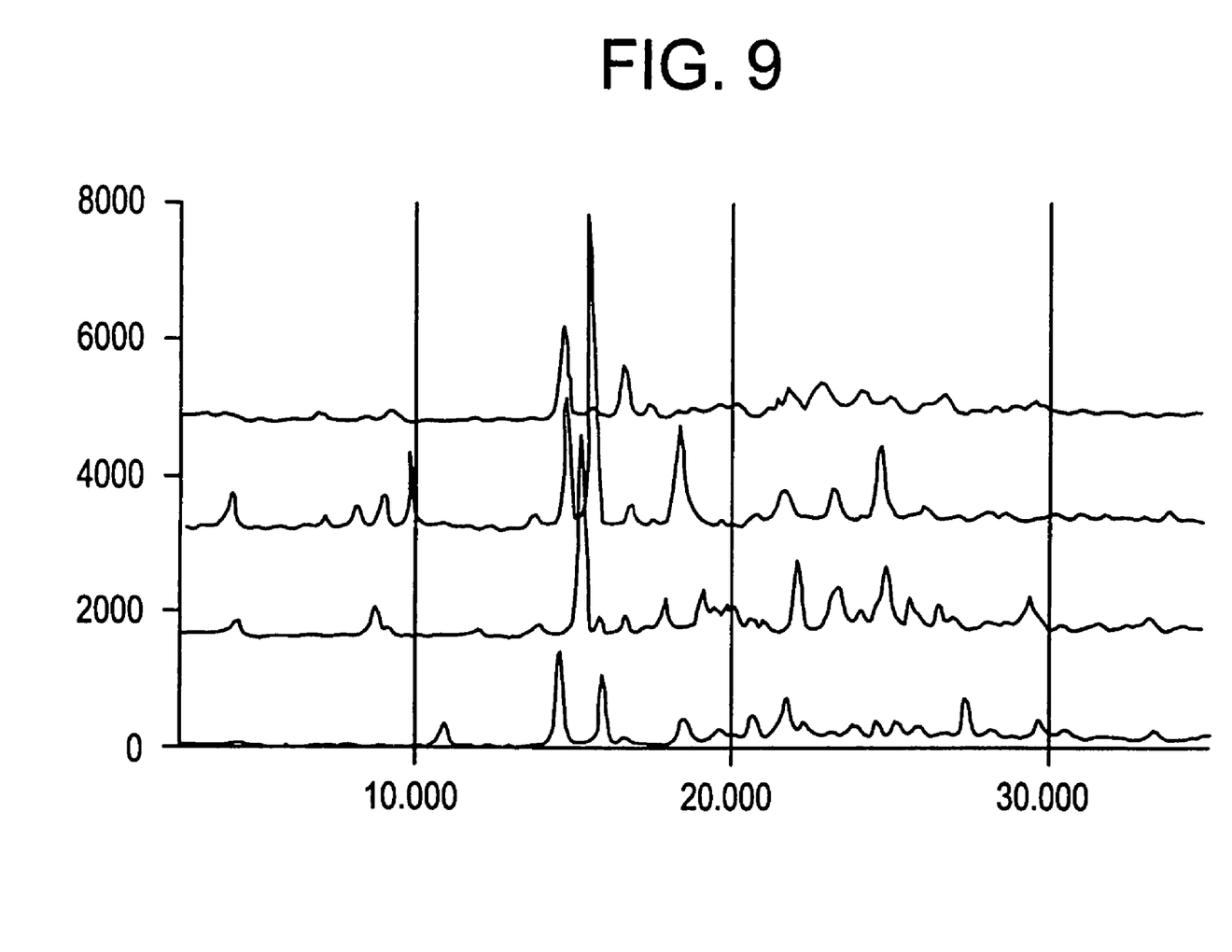
FIG. 9 is the multi-plot of X-ray diffraction patterns of Forms I, II, III and IV
Figure 13:
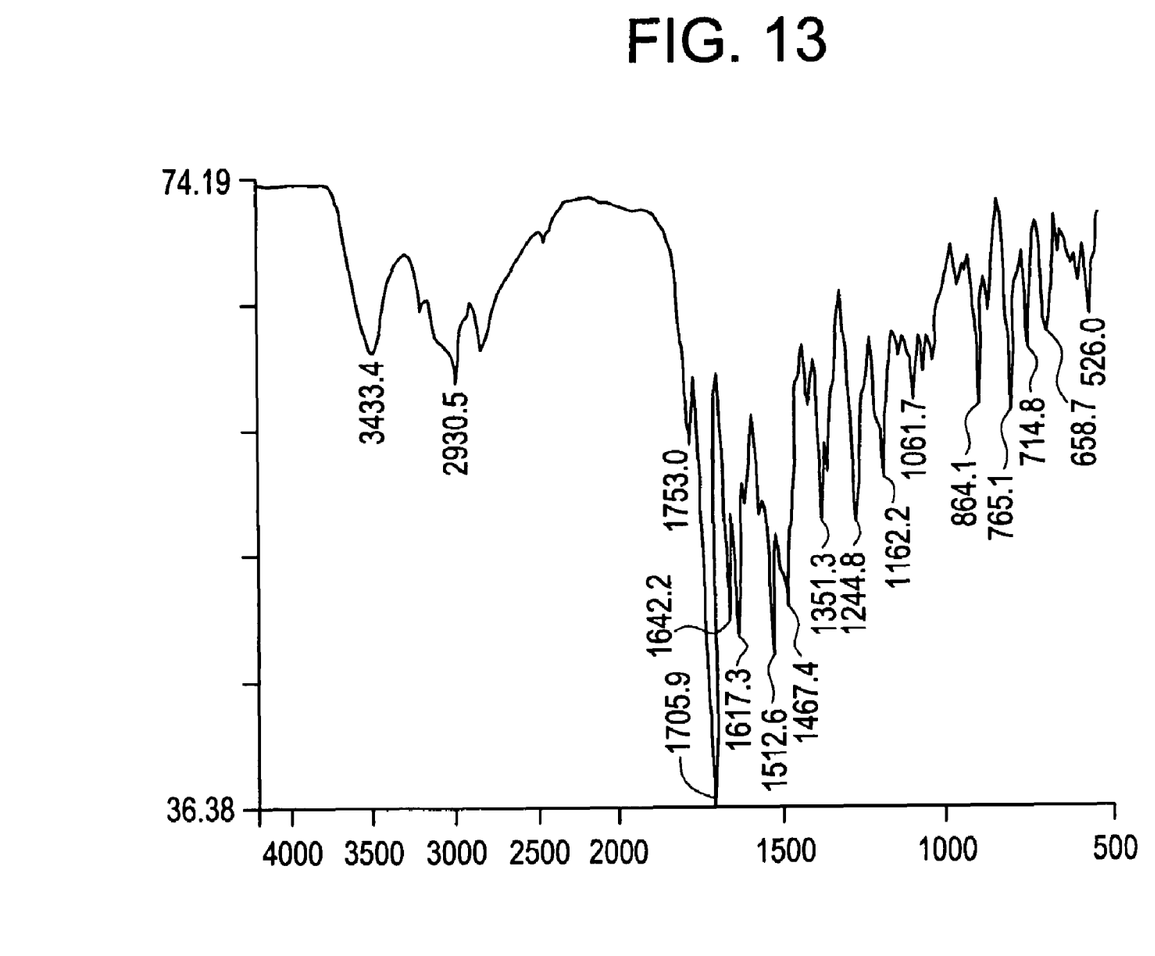
FIG. 13 is a characteristic infrared absorption spectrum of Form IV in potassium bromide.

According to yet another feature of the present invention, there is provided a novel polymorphic Form-IV of 5-[4-[2-[N-methyl-N-(2-pyridyl)amino]ethoxy]benzyl] thiazolidine-2,4-dione maleate, and its stereoisomers having the formula I which is characterized by the following data:

DSC: Endotherm at 125.39° C. (on set at 121.03° C.) (FIG. 4).

XRD (2Θ): 7.4, 8.8, 9.54, 14.98, 15.32, 15.82, 16.90, 17.70, 18.40, 18.54, 19.08, 19.72, 20.22, 20.48, 21.36, 21,66, 22.18, 22.58, 23.32, 23.96, 24.52, 25.38, 26.48, 27.00, 27.58, 27.94, 28.34, 28.54, 28.84, 29.10, 29.86, 30.02, 30.40, 30.52, 30.84, 31.40, 31.94 (FIG. 8).

IR: 3433 (m), 2930 (m), 1753 (w), 1705 (s), 1642 (w), 1617 (m), 1512 (s), 1467 (w), 1351 (m), 1244 (m), 1162 (m), 1061 (w), 864 (s), 765 (s), 714 (w), 658 (m), 526 (w) (FIG. 13).

According to another feature of the present invention, there is provided a process for the preparation of novel polymorphic Form-I of 5-[4-[2-[N-methyl-N-(2-pyridyl) amino]ethoxy]benzyl]thiazolidine-2,4-dione maleate, of the formula I, having the characteristics described earlier, which comprises:
(i) synthesizing 5-[4-[2-[N-methyl-N-(2-pyridyl)amino] ethoxy]benzyl]thiazolidine-2,4-dione maleate, employing known methods and dissolving in ethanol,
(ii) heating the solution in a steam bath till the solid completely dissolved,
(iii) filtering the clear solution and cooling to room temperature over a period of 18 h,
(iv) isolating the Form I of 5-[4-[2-[N-methyl-N-(2-pyridyl)amino]ethoxy]benzyl]thiazolidine-2,4-dione maleate formed.

According to another feature of the present invention, there is provided a process for the preparation of novel polymorphic Form-II of 5-[4-[2-[N-methyl-N-2-pyridyl) amino]ethoxy]benzyl]thiazolidine-2,4-dione maleate, of the formula I, having the characteristics described earlier, which comprises:
(i) synthesizing 5-[4-[2-[N-methyl-N-(2-pyridyl)amino] ethoxy]benzyl]thiazolidine-2,4-dione maleate, employing known methods and dissolving in acetone,
(ii) heating the solution in a steam bath till the solid completely dissolved,
(iii) filtering the clear solution and cooling to room temperature over a period of 18 h,
(iv) isolating the Form II of 5-[4-[2-[N-methyl-N-(2-pyridyl)amino]ethoxy]benzyl]thiazolidine-2,4-dione maleate formed.

According to another feature of the present invention, there is provided a process for the preparation of novel polymorphic Form-III of 5-[4-[2-[N-methyl-N-(2-pyridyl) amino]ethoxy]benzyl]thiazolidine-2,4-dione maleate, of the formula I, having the characteristics described earlier, which comprises:
(i) synthesizing 5-[4-[2-[N-methyl-N-(2-pyridyl)amino] ethoxy]benzyl]thiazolidine- 2,4-dione maleate, employing known methods and dissolving in methanol,
(ii) heating the solution in a steam bath till the solid completely dissolved,
(iii) filtering the clear solution and cooling to room temperature over a period of 18 h,
(iv) isolating the Form m of 5-[4-[2-[N-methyl-N-(2-pyridyl)amino]ethoxy]benzyl]thiazolidine-2,4-dione maleate formed.

According to yet another feature of the present invention, there is provided a process for the preparation of novel polymorphic Form-IV of 5-[4-[2-[N-methyl-N-(2-pyridyl) amino]ethoxy]benzyl]thiazolidine-2,4-dione maleate of the formula I, having the characteristics described earlier, which comprises:
(i) synthesizing 5-[4-[2-[N-methyl-N-(2-pyridyl)amino] ethoxy]benzyl]thiazolidine-2,4-dione maleate, employing known methods and dissolving in 1,4-dioxane,
(ii) heating the solution in a steam bath till the solid completely dissolved,
(iii) filtering the clean solution and cooling to room temperature over a period of 18 h,
(iv) isolating the Form IV of 5-[4-[2-[N-methyl-N-(2-pyridyl)amino]ethoxy]benzyl]thiazolidine-2,4-dione maleate formed.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981. Conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

The present invention also envisages a pharmaceutical composition comprising any of the polymorphic Forms I to IV of 5-[4-[2-[N-methyl-N-(2-pyridyl)amino]ethoxy]benzyl]thiazolidine-2,4-dione maleate, of the formula (I) and a pharmaceutically acceptable carrier.

The present invention also envisages a pharmaceutical composition comprising a mixture of any of polymorphic Forms I to IV of 5-[4-[2-[N-methyl-N-(2-pyridyl) amino] ethoxy]benzyl]thiazolidine-2,4-dione maleate, of the formula (I) and a pharmaceutically acceptable carrier.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active ingredient, the remainder of the composition being pharmaceutically acceptable carriers, diluents or solvents.

The polymorphic forms of the formula (I) as defined above are clinically administered to mammals, including man, via either oral, nasal, pulmonary, transdermal or parenteral rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the polymorphic form can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the polymorphic form can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the polymorphic forms of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed.

A typical tablet production method is exemplified below:

Tablet Production Example:

| a) | 1) Active ingredient | 30 g |
|---|---|---|
| | 2) Lactose | 95 g |
| | 3) Corn starch | 30 g |
| | 4) Carboxymethyl cellulose | 44 g |
| | 5) Magnesium stearate | 1 g |
| | | 200 g for 1000 tablets |

The ingredients 1 to 3 are uniformly blended with water and granulated after drying under reduced pressure. The ingredient 4 and 5 are mixed well with the granules and compressed by a tabletting machine to prepare 1000 tablets each containing 30 mg of active ingredient.

| b) | 1) Active ingredient | 30 g |
|---|---|---|
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g for 1000 tablets |

The ingredients 14 are uniformly moistened with an aqueous solution of 5 and granulated after drying under reduced pressure. Ingredient 6 is added and granules are compressed by a tabletting machine to prepare 1000 tablets containing 30 mg of ingredient 1.

The present invention is described in detail in the examples given below which are provided by way of illustration only and therefore should not be construed to limit the scope of the invention.

EXAMPLES

Example 1

A mixture of 5-[4-[2-[N-methyl-N-2-pyridyl)amino] ethoxy]benzyl]thiazolidine-2,4-dione (69 g, 0.19 M) and maleic acid (22.8 g, 0.19 M) was heated under reflux while stirring in iso-propanol (1.0 L) until a clear solution was obtained (1-2 h). The reaction mass was allowed to cool to RT while stirring for 15-20 h. The white to off-white crystalline compound was filtered, washed with iso-propanol (3×100 ml) and pet. ether (2×100 ml) dried to furnish white to off-white product (84.5 g; Yield: 92%).

Example 2

1 g of the 5-[4-[2-[N-methyl-N-(2-pyridyl)amino]ethoxy]benzyl]thiazolidine-2,4-dione maleate obtained by the process as described in Example-1 was taken in 10 ml EtOH and heated on a steam bath till the solid completely dissolved. The clear solution was allowed to cool to RT over a period of 18 h to yield 80% of >99% pure polymorphic Form I of 5-[4-[2-[N-methyl-N-(2-pyridyl)amino]ethoxy]benzyl]thiazolidine-2,4-dione maleate.

Example 3

1 g of the 5-[4-[2-[N-methyl-N-(2-pyridyl)amino]ethoxy]benzyl]thiazolidine-2,4-dione maleate obtained by the process as described in Example-1 was taken in 50 ml acetone and heated on a steam bath till the solid completely dissolved. The solution was allowed to cool to RT over a period of 18 h to yield 60% of >99% pure polymorphic Form II of 5-[4-[2-[N-methyl-N-(2-pyridyl)amino]ethoxy]benzyl]thiazolidine-2,4-dione maleate.

Example 4

1 g of the 5-[4-[2-[N-methyl-N-(2-pyridyl)amino]ethoxy]benzyl]thiazolidine-2,4-dione maleate obtained by the process as described in Example-1 was dissolved in 10 ml of methanol and heated on a steam bath till the solid completely dissolved. The clear solution was filtered and allowed to cool to RT over a period of 18 h to yield 75% of >99% pure polymorphic Form III of 5-[4-[2-[N-methyl-N-(2-pyridyl)amino]ethoxy]benzyl]thiazolidine-2,4-dione maleate.

Example 5

1 g of the 5-[4-[2-[N-methyl-N-(2-pyridyl)amino]ethoxy]benzyl]thiazoidine-2,4-dione maleate obtained by the process as described in Example-1 was taken in 10 ml 1,4-dioxane and heated on a steam bath till the solid completely dissolved. The clear solution was allowed to cool to RT over a period of 18 h to yield 70% of >99% pure polymorphic Form IV of 5-[4-[2-[N-methyl-N-(2-pyridyl)amino]ethoxy]benzyl]thiazolidine-2,4-dione maleate.

What is claimed is:

1. A polymorphic Form-I of 5-[4-[2-[N-methyl-N-(2-pyridyl) amino]ethoxy]benzyl]thiazolidine-2,4-dione maleate, having the formula I and having a differential scanning calorimetry endotherm at 100.53° C. and an onset at 88.65° C.

2. A polymorphic Form-II of 5-[4-[2-[N-methyl-N-(2-pyridyl) amino]ethoxy]benzyl]thiazolidine-2,4-dione maleate, having the formula I and having a differential scanning calorimetry endotherm at 127.67° C. and an onset at 123.17° C.

3. A polymorphic Form-III of 5-[4-[2-[N-methyl-N-(2-pyridyl)amino]ethoxy]benzyl]thiazolidine-2,4-dione maleate having the formula I and having a differential scanning calorimetry endotherm at 126.41° C. and an onset at 122.06° C.

4. A polymorphic Form-IV of 5-[4-[2-[N-methyl-N-(2-pyridyl)amino]ethoxylbenzyl]thiazolidine-2,4-dione maleate, having the formula I and having a differential scanning calorimetry endotherm at 125.39° C. and an onset at 121.03° C..

5. A process for the preparation of polymorphic Form I of 5-[4-[2-[N-methyl-N-(2-pyridyl) amino]ethoxy]benzyl]thiazolidine-2,4-dione maleate, which comprises
   (i) mixing 5-[4-[2-[N-methyl-N-(2-pyridyl )amino]ethoxy]benzyl]thiazolidine-2,4-dione maleate, with ethanol,
   (ii) heating the mixture to form a solution,
   (iii) cooling to room temperature and
   (iv) recovering crystals of Form I of 5-[4-[2-[N-methyl-N-(2-pyridyl)amino]ethoxy]benzyl]thiazolidine-2,4-dione maleate.

6. A process for the preparation of polymorphic Form II of 5-[4-[2-[N-methyl N-(2-pyridyl )amino]ethoxy]benzyl]thiazolidine-2,4-dione maleate, which comprises:
   (i) mixing 5-[4-[2-[N-methyl-N-(2-pyridyl )amino]ethoxy]benzyl]thiazolidine-2,4-dione maleate, with acetone, (ii) heating the mixture to form a solution,
(iii) cooling to room temperature and
(iv) recovering crystals of Form II of 5-[4-[2-[N-methyl-N-(2-pyridyl)amino]ethoxy]benzyl]thiazolidine-2,4-dione maleate.

7. A process for the preparation of polymorphic Form III of 5-[4-[2-[N methyl-N-(2-pyridyl )amino]ethoxy]benzyl]thiazolidine-2,4-dione maleate, which comprises:
   (i) mixing 5-[4-[2-[N-methyl-N-(2-pyridyl )amino] ethoxy]benzyl]thiazolidine-2,4-dione maleate, with methanol,
   (ii) heating the mixture to form a solution,
   (iii) cooling to room temperature and
   (iv) recovering crystals of Form III of 5-[4-[2-[N-methyl-N-(2-pyridyl)amino]ethoxy]benzyl]thiazolidine-2,4-dione maleate.

8. A process for the preparation of polymorphic Form IV of 5-[4-[2-[N methyl-N-(2-pyridyl )amino]ethoxy]benzyl]thiazolidine-2,4-dione maleate, which comprises:
   (i) mixing 5-[4-[2-[N-methyl-N-(2-pyridyl)amino] ethoxy]benzyl]thiazolidine-2,4-dione maleate, with 1,4-dioxane,
   (ii) heating the mixture to form a solution,
   (iii) cooling to room temperature and
   (iv) recovering crystals of Form IV of 5-[4-[2-[N-methyl-N-(2-pyridyl)amino]ethoxy]benzyl]thiazolidine-2,4-dione maleate.

9. The polymorphic form of claim 1, having an X-ray powder diffraction pattern comprising peaks at 2θ angles of 10.90, 14.54, 15.96, 18.46, 18.60, 19.76, 20.72, 21.84, 22.36, 22.46, 23.90, 24.04, 24.72, 25.30, 25.98, 27.44, and 29.70 degrees.

10. The polymorphic form of claim 1, having an infrared absorption spectrum comprising peaks at 3435, 2997, 2773, 1750, 1701, 1620, 1510, 1362, 1332, 1237, 1165, 864, 764, 717, 654, and 540 $cm^{-1}$.

11. The polymorphic form of claim 2, having an X-ray powder diffraction pattern comprising peaks at 2θ angles of 8.90, 15.40, 18.06, 19.20, 22.30, 23.40, 23.62, 24.80, 25.10, 25.84, 26.72, 27.18, 29.30, 29.54, 29.84, and 33.26 degrees.

12. The polymorphic form of claim 2, having an infrared absorption spectrum comprising peaks at 3424, 3040, 2947, 2720, 1751, 1702, 1641, 1618, 1574, 1541, 1412, 1382, 1359, 1326, 1265, 1242, 1213, 1162, 1067, 1031, 865, 773, 713, 667, 576, and 539 $cm^{-1}$.

13. The polymorphic form of claim 3, having an X-ray powder diffraction pattern comprising peaks at 2θ angles of 4.60, 8.46, 9.24, 14.98, 15.86, 17.02, 18.60, 21.92, 23.50, 25.00, 25.44, 26.00, 26.38, 28.34, and 33.90 degrees.

14. The polymorphic form of claim 3, having an infrared absorption spectrum comprising peaks at 3429, 2949, 2738, 1747, 1704, 1641, 1617, 1513, 1464, 1352, 1244, 1178, 1069, 862, 777, 717, 657, and 589 $cm^{-1}$.

15. The polymorphic form of claim 4, having an X-ray powder diffraction pattern comprising peaks at 2θ angles of 7.4, 8.8, 9.54, 14.98, 15.32, 15.82, 16.90, 17.70, 18.40, 18.54, 19.08, 19.72, 20.22, 20.48, 21.36, 21.66, 22.18, 22.58, 23.32, 23.96, 24.52, 25.38, 26.48, 27.00, 27.58, 27.94, 28.34, 28.54, 28.84, 29.10, 29.86, 30.02, 30.40, 30.52, 30.84, 31.40, and 31.94 degrees.

16. The polymorphic form of claim 4, having an infrared absorption spectrum comprising peaks at 3433, 2930, 1753, 1705, 1642, 1617, 1512, 1467,1351,1244,1162, 1061, 864, 765, 714, 658, and 526 $cm^{-1}$.

* * * * *